(12) United States Patent
Melsheimer

(10) Patent No.: US 8,287,558 B2
(45) Date of Patent: Oct. 16, 2012

(54) INSIDE OUT T-FASTENER SYSTEM

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/204,311

(22) Filed: Aug. 5, 2011

(65) Prior Publication Data

US 2011/0288488 A1 Nov. 24, 2011

Related U.S. Application Data

(62) Division of application No. 11/870,946, filed on Oct. 11, 2007, now abandoned.

(60) Provisional application No. 60/854,592, filed on Oct. 26, 2006.

(51) Int. Cl.
*A61B 17/08* (2006.01)
(52) U.S. Cl. ........................................ 606/153; 606/232
(58) Field of Classification Search .......................... None
See application file for complete search history.

(56) References Cited

U.S. PATENT DOCUMENTS

| | | | |
|---|---|---|---|
| 4,665,906 A | 5/1987 | Jervis | |
| 5,123,914 A | 6/1992 | Cope | |
| 5,151,086 A * | 9/1992 | Duh et al. | 604/506 |
| 5,318,543 A * | 6/1994 | Ross et al. | 604/170.01 |
| 5,350,385 A | 9/1994 | Christy | |
| 5,429,598 A * | 7/1995 | Waxman et al. | 604/506 |
| 5,531,678 A * | 7/1996 | Tomba et al. | 606/142 |
| 5,545,141 A * | 8/1996 | Eld | 604/170.03 |
| 5,626,614 A * | 5/1997 | Hart | 606/232 |
| 5,741,278 A | 4/1998 | Stevens | |
| 6,425,887 B1 | 7/2002 | McGuckin et al. | |
| 6,491,707 B2 | 12/2002 | Makower et al. | |
| 6,592,559 B1 | 7/2003 | Pakter et al. | |
| 7,056,325 B1 | 6/2006 | Makower et al. | |
| 8,092,472 B2 * | 1/2012 | Cerier | 606/139 |
| 2005/0216042 A1 * | 9/2005 | Gertner | 606/151 |
| 2005/0251176 A1 * | 11/2005 | Swanstrom et al. | 606/153 |
| 2007/0073320 A1 * | 3/2007 | Mikkaichi et al. | 606/153 |
| 2008/0269781 A1 * | 10/2008 | Funamura et al. | 606/138 |
| 2009/0157099 A1 | 6/2009 | Surti | |

OTHER PUBLICATIONS

COOK Diagnostic and Interventional Products Catalog entitled "Products for Gastroenterology", (18) pages. Copyright Cook Incorporated 2000.

* cited by examiner

*Primary Examiner* — Corrine M McDermott
*Assistant Examiner* — Todd J Scherbel
(74) *Attorney, Agent, or Firm* — Brinks Hofer Gilson & Lione

(57) ABSTRACT

A medical device for providing wall apposition of two bodily walls in accordance with the teachings of the present invention. The medical device is used at a previously formed puncture site having perforations formed in the walls. By way of example, the two walls are described herein as the abdominal and gastric walls, although it will be recognized that any two bodily walls may be fastened together utilizing the medical device and the methods described herein. It will also be understood that the procedures described herein may be performed using image guidance such as fluoroscopy, although the device and method may readily be performed without such assistance.

15 Claims, 9 Drawing Sheets

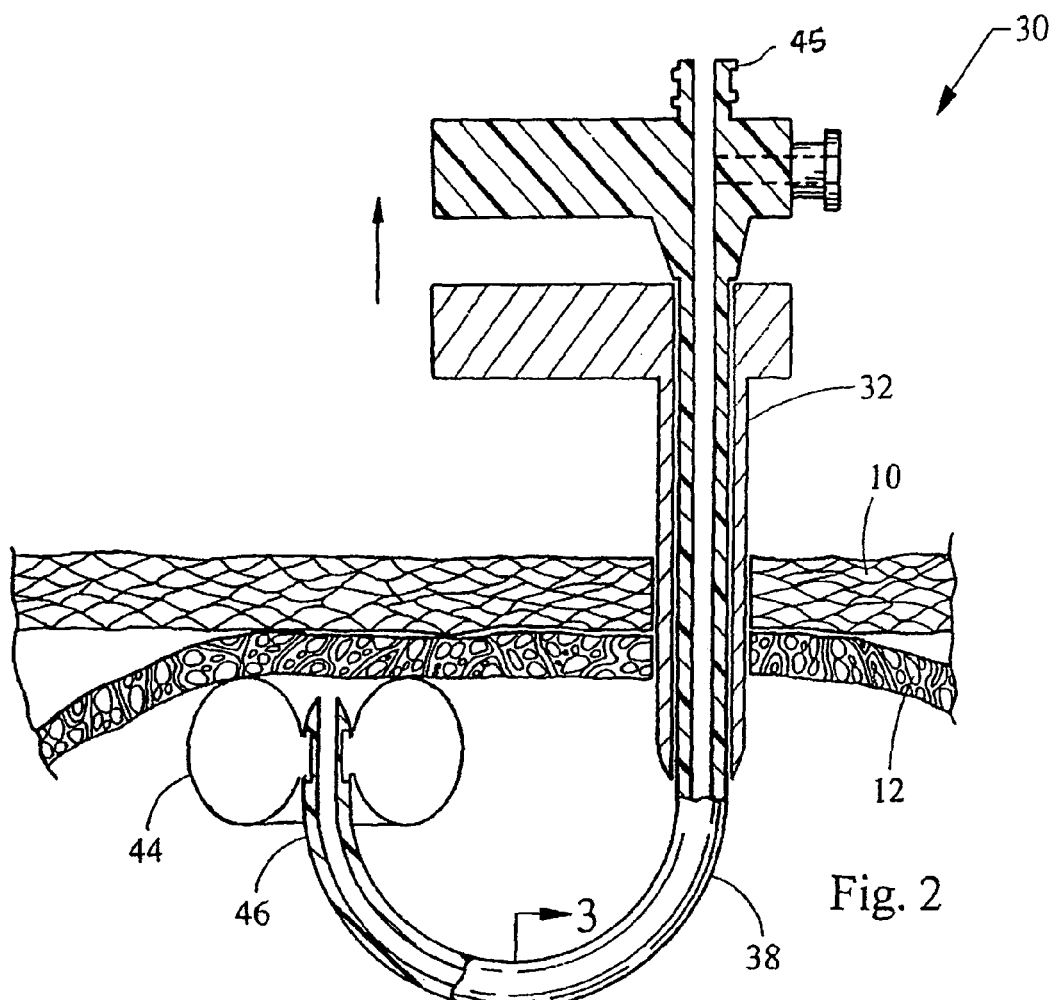
Fig. 2
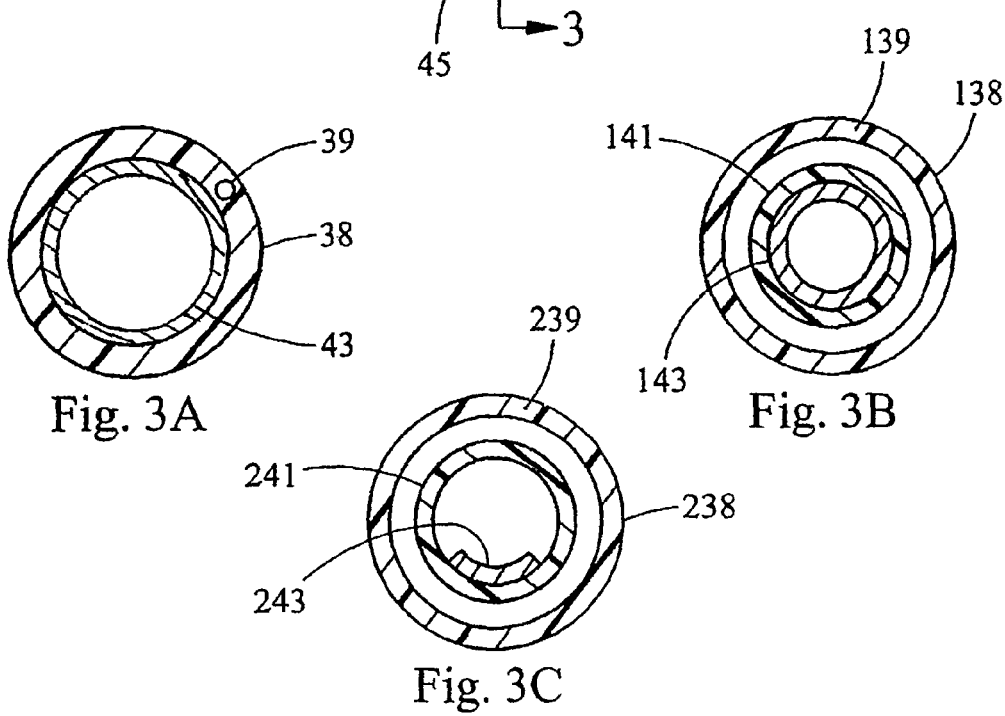
Fig. 3A  Fig. 3B
Fig. 3C

INSIDE OUT T-FASTENER SYSTEM

CROSS-REFERENCE TO RELATED APPLICATIONS

This application is a divisional of U.S. patent application Ser. No. 11/870,946 filed on Oct. 11, 2007, now abandoned, which claims the benefit U.S. Provisional Application Ser. No. 60/854,592 filed on Oct. 26, 2006, entitled "INSIDE OUT T-FASTENER SYSTEM", the entire contents of which are incorporated herein by reference.

FIELD OF THE INVENTION

The present invention relates generally to medical devices and procedures for wall apposition utilizing tissue fasteners such as "T-fasteners" or "T-anchors", and more particularly relates to percutaneous image-guided placement of such fasteners and gastrostomy tubes.

BACKGROUND OF THE INVENTION

The percutaneous image-guided placement of gastrostomy tubes is generally considered safer than endoscopic or surgical placement, but is usually limited to smaller diameter gastrostomy tubes and/or the use of T-fasteners so as not to push the gastric wall away from the abdominal wall. It has been found that one difficulty in using T-fasteners in this manner is that the fasteners sometimes go into the abdominal wall at unfavorable angles, or with unfavorable spacing, such that their efficacy is compromised or an excessive number of T-fasteners are necessary to place the tube.

BRIEF SUMMARY OF THE INVENTION

A medical device and method is provided for obtaining wall apposition of two bodily walls which reliably and accurately places fasteners at favorable angles, and in a controllable pattern that minimizes the number of fasteners required. The medical device generally includes an access cannula, a guide tube, and a flexible puncturing device. The guide tube is sized to be slidably received by the access cannula and is operable between a first linear configuration and a second non-linear configuration. The flexible puncturing device is sized to be slidably received by the guide tube. The method for providing apposition of two bodily walls utilizes this medical device and generally comprises the steps of forming a puncture site through the two walls, inserting the access cannula into the puncture site, passing the guide tube through the outer cannula, positioning a distal end of the guide tube proximate one of the walls, passing the flexible puncturing device through the guide tube and puncturing the two walls, connecting a fastener to the puncture device, retracting the puncture device to draw the fastener through the two walls, and securing the fastener to maintain apposition of the two walls.

According to more detailed aspects, the guide tube retroflexes in the second configuration for engagement of one of the bodily walls. A distal end of the guide tube in the second configuration is thus laterally spaced from the access cannula and is generally rotated about 180 degrees relative to its position in the first configuration. The guide tube is preferably formed of a shape memory material, and may either be biased towards the second non-linear configuration, or may be temperature dependent. In the latter case, the transition temperature is at about body temperature. In the former case, the access cannula is rigid and is used to straighten the guide tube into the first linear configuration. A distal end of the guide tube preferably includes an inflatable balloon for engagement of one of the bodily walls.

According to other additional features of the present invention, the positioning of the guide tube includes advancing and retracting the guide tube to engage one of the walls at a desired location. After placement of one fastener, the guide tube may be advanced to disengage the bodily wall, rotated (about an axis of the access cannula), and then retracted to position a distal end of the guide tube at a location spaced from the previously placed fastener. The steps may be repeated with a plurality of fasteners, resulting in a generally circular configuration of fasteners around the primary puncture site. One of many possible uses of the medical device and method is to obtain wall apposition of the abdominal and gastric walls, wherein the primary puncture site is used for placement of a gastrostomy tube.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 2 is a cross-sectional view of the medical device depicted in FIG. 1A, showing its guide tube in a second configuration;

FIG. 3A is a cross-sectional view taken about the line 3-3 in FIG. 2, while FIG. 3B and FIG. 3C are cross-sectional views similar to FIG. 3A but showing alternate embodiments of the medical device constructed in accordance with the teachings of the present invention;

DETAILED DESCRIPTION OF THE INVENTION

Figure 1A:
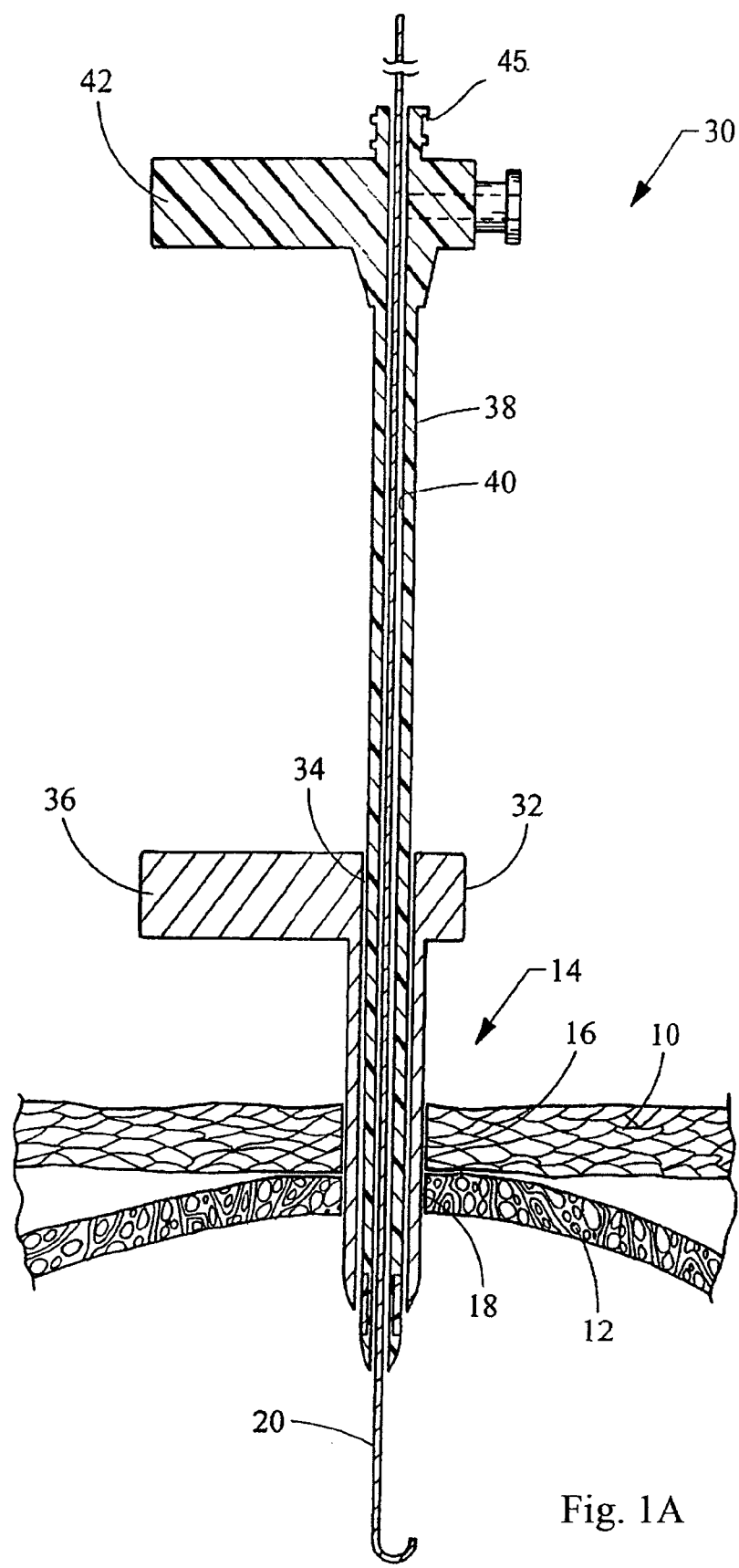
FIG. 1A is a cross-sectional view of a medical device constructed in accordance with the teachings of the present invention.

Turning now to the figures, FIGS. 1A-1C and 2 depict an embodiment of a medical device 30 for providing wall apposition of two bodily walls 10, 12 in accordance with the teachings of the present invention. The medical device 30 is used at a previously formed puncture site 14 having perforations 16, 18 formed in the walls, 10, 12, respectively. By way of example, the two walls 10, 12 are described herein as the abdominal and gastric walls, although it will be recognized that any two bodily walls may be fastened together utilizing the medical device 30 and the methods described herein. It will also be understood that the procedures described herein may be performed using image guidance such as fluoroscopy, although the device and method may readily be performed without such assistance.

To form the puncture site 14, a puncture device such a needle or a trocar is utilized to initially pass through the abdominal and gastric walls, 10, 12, and then deliver a wire guide 20 therethrough, although any known or future cutting means may be utilized. Various dilators (not shown) may be used to enlarge the initial openings to a size sufficient to receive the medical device 30. For example, an initial 16 gauge puncture needle may be utilized, which is then enlarged with dilators to approximately 20 french, for receiving the medical device 30.

Figure 4:
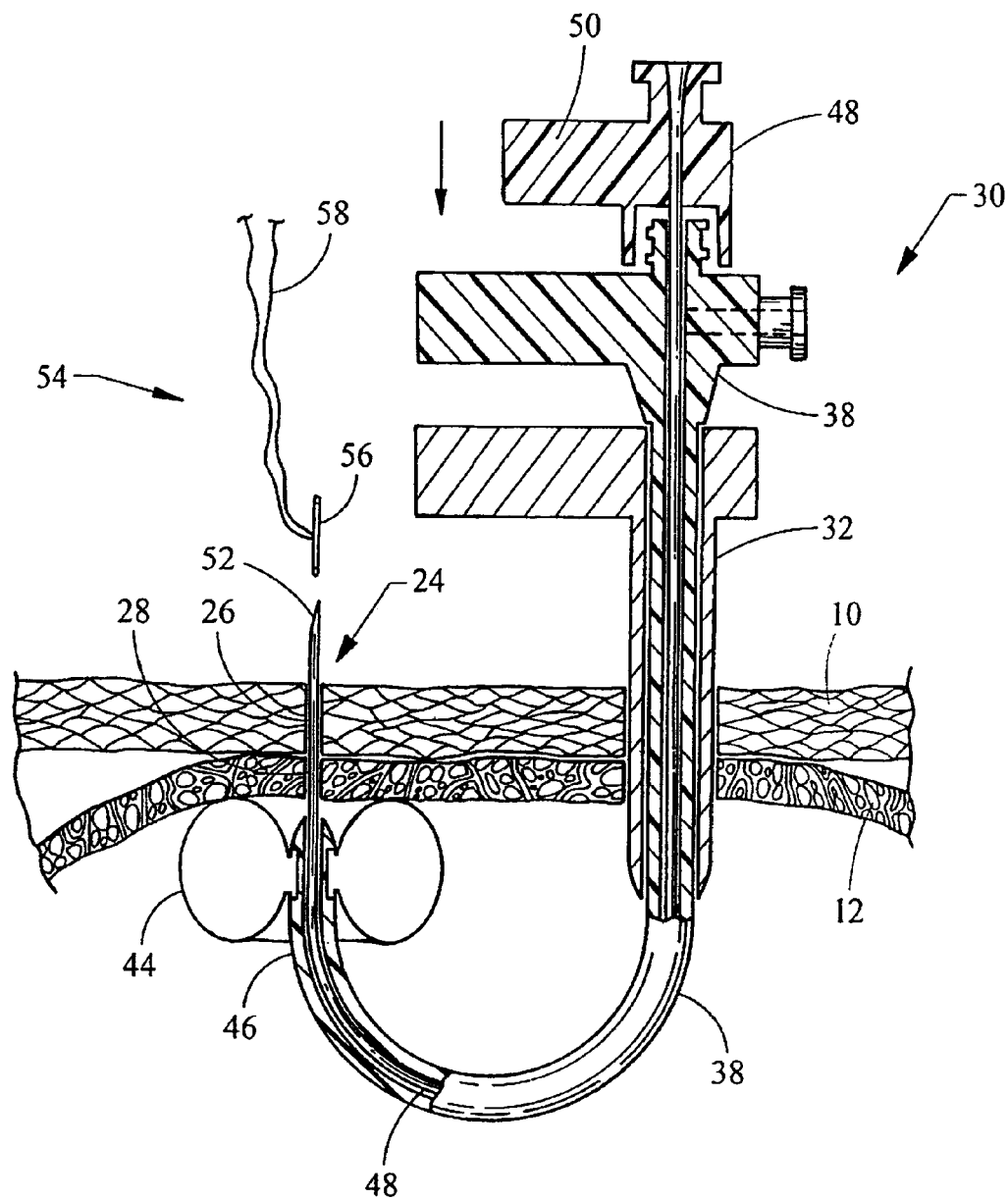
FIGS. 4-6 illustrate the placement of a fastener utilizing the medical device depicted in FIG. 1A.

The medical device 30 generally includes an access cannula 32, a guide tube 38 and a flexible puncturing device 48 (FIG. 4). The access cannula 32 and guide tube 38 may be placed over the wire guide 20, and the wire guide 20 is then removed. A loading dilator may be used during the initial access to take up the space between guide tube 38 and the wire guide 20 (or between guide tube 38 and puncture needle). The access cannula 32 defines an interior lumen 34 for receiving the guide tube 38, and may also include a handle 36 at its proximal end for providing easy manipulation thereof. The access cannula 32 is preferably formed of a rigid and dimensionally stable material, such as stainless steel or another metal, although this is not a necessary requirement and the access cannula can be flexible.

Once the access cannula 32 and guide tube 38 are positioned within the puncture site 14, the guide tube 38 may then be advanced relative to the access cannula 32, as shown in FIG. 2. The guide tube 38 also defines an interior lumen 40 and includes a handle 42 at its proximal end to facilitate manipulation and translation of the guide tube 38 relative to the access cannula 32. The handle 42 includes threaded connector 45 for attachment various instruments or devices such as the aforementioned dilator. The guide tube 38 is operable between a first linear configuration as depicted in FIG. 1A and a second non-linear configuration such as depicted in FIG. 2. In one preferred construction, the guide tube 38 is formed (at least in part) of a shape memory material such as nitinol or other similar alloys. As such, the guide tube 38 will be temperature dependent and is designed to transition between the first and second configurations at about body temperature. For example, the guide tube 38 is introduced into the patient at a temperature below body temperature and is a first entry. As the guide tube 38 is warmed to body temperature, it then assumes the second configuration.

In the second configuration, a distal portion 45 of the guide tube 38 retroflexes so that the distal end 46 faces the interior surface of the gastric wall 12. Thus, the distal end 46 of the guide tube 38 has been generally rotated about 180 degrees from the first configuration to the second configuration. The device 30 (or at least the guide tube 38) is then retracted so that the gastric wall 12 is engaged from the interior by the distal end 46 of the guide tube 38 for subsequent placement of a fastener at the engaged location. It will be recognized that the radius of curvature in the distal portion 45 in the second configuration, as well as the degree of bend (i.e. between 0 and 180 degrees) may be tailored for specific procedures and patients.

In another preferred construction, the guide tube is simply constructed of a resilient material such as nitinol, stainless steel, other metals or alloys, or resilient plastics, and is biased towards the second configuration. In this case, the outer access cannula 32 is utilized to straighten the guide tube 38 into its first linear configuration, and thus the access cannula 32 is sufficiently rigid to straighten the guide tube 38. In either case, upon a distal end 46 of the guide tube 38 passing beyond a distal end of the access cannula 32 and into the gastric lumen, the second configuration of the guide tube 38 is obtained. It will be recognized that numerous other structures and designs of the guide tube 38 can be utilized to achieve the same effect, such as a segmented tube where the segments are controllably rotatable relative to each other by for example, a control wire operably connected along one side of the segments. It will also be recognized that the access cannula 32 and guide tube 38 can have non-circular cross-sections. The access cannula 32 may also have some curvature at its distal end to facilitate the placement of guide tube 38 and the fasteners.

Figure 1B:
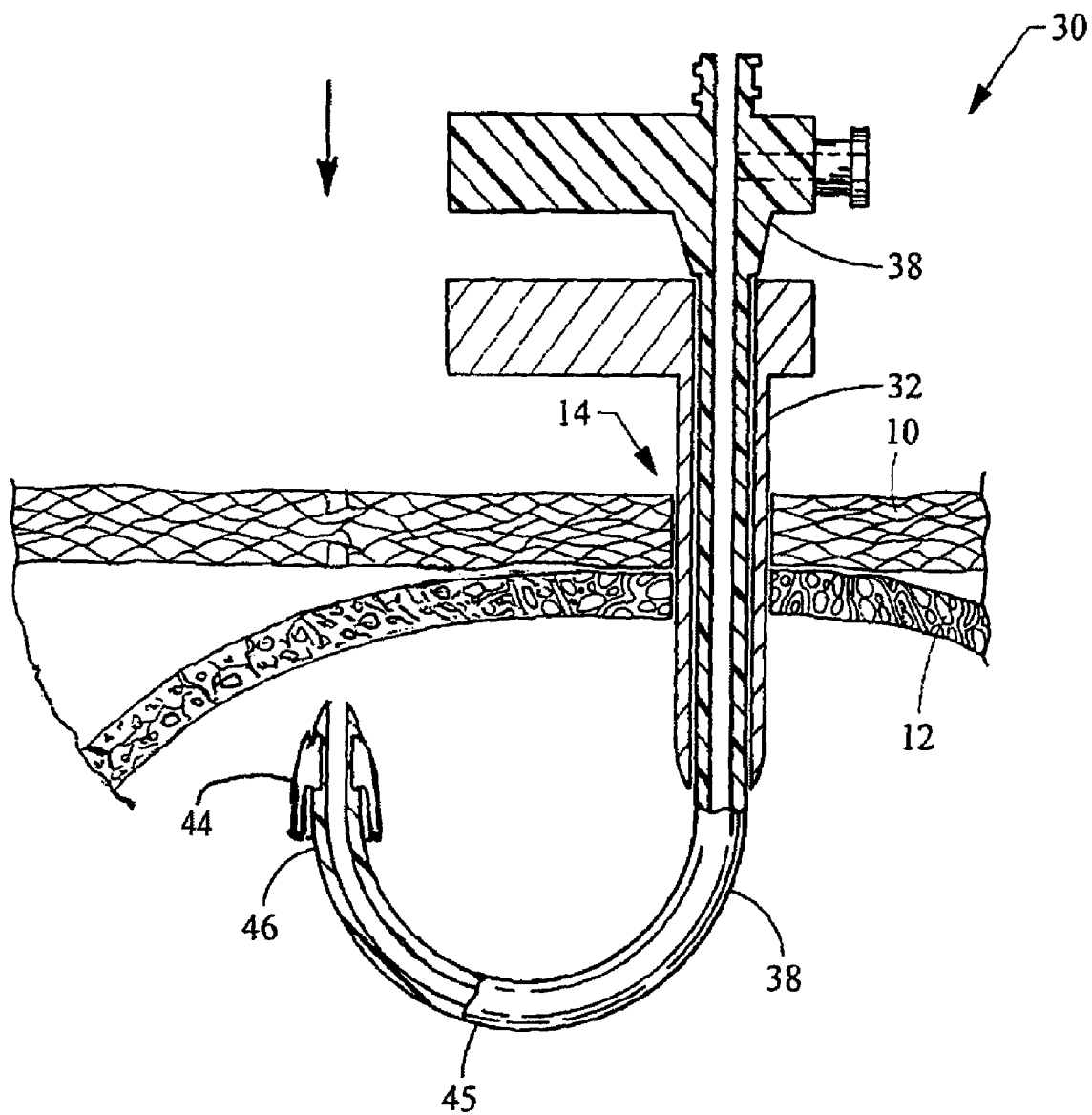
FIGS. 1B and 1C illustrate deployment of the medical device in FIG. 1A.
Figure 1C:
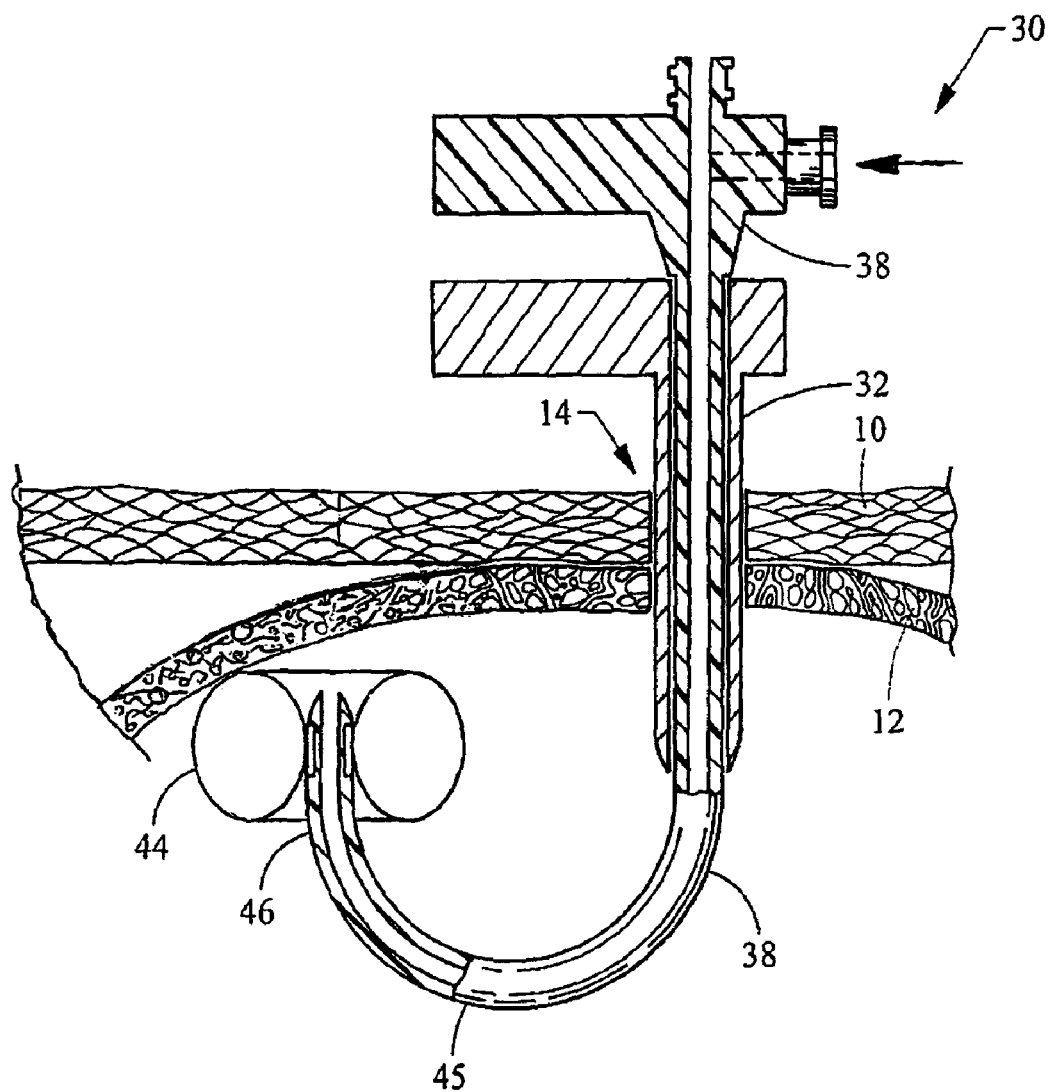

The guide tube 38 also preferably includes an inflatable balloon 44 located at its distal end 46 for engaging the gastric wall 12 or other bodily wall. As shown in FIGS. 1B and 1C, once the distal end 46 of the guide tube 38 is advanced beyond the access cannula 32, the balloon 44 may be operated from a deflated state (FIG. 1B) to an inflated state (FIG. 1C). The balloon 44 may be compliant or non-compliant, and provides an enlarged surface for engaging and positioning the gastric wall 12. As best seen in FIG. 3A, the guide tube 38 includes an inflation lumen 39 leading to the inflatable balloon 44. A nitinol tube 43 is securely fit within the primary lumen 41 defined by the guide tube 38. Alternatively, and as shown in FIG. 3B, the guide tube 138 may be formed of a dual lumen tube, i.e. having an outer wall 139 and an inner wall 141 defining an inflation channel therebetween for inflating the balloon 144. The outer and inner walls 139, 141 may be constructed of a flexible plastic, while a nitinol tube 143 is securely fit within the inner wall 141 as shown. Another alternate embodiment of the guide tube 238 is shown in FIG. 3C. Again, an outer wall 139 and an inner wall 141 are oriented to define an inflation passageway therebetween. However, in this embodiment a simple strip 243 of shape-memory material such as nitinol is connected to the inner wall 241 for providing operability between the first linear configuration (FIG. 1A) and the second non-linear configuration (FIG. 2). It will be recognized that numerous other designs may readily be employed for providing a dual lumen guide tube having this operability, such as over molding the inner wall 41 over the shape memory material, or even forming the outer and inner walls 39, 41 of nitinol material and simply connecting the inflatable balloon 44 at the distal end of the nitinol guide tube 38.

Radiographic materials may also be formed in or attached to the distal end 46 of the guide tube 38 to assist with fluoroscopic guidance of T-fastener placement. Likewise, the distal end 46 of the guide tube 38 can includes materials and surfaces having enhanced ultrasonic reflectivity, such by being roughened, having dimples or other incongruities, or having embedded particles. It will be recognized that, in addition to fluoroscopy and ultrasound guidance, various other visualization or image guidance systems may be employed. Tactile or visual observation may also be used in conjunction with manipulation of the guide tube 38 to determine placement of T-fasteners.

The inflatable balloon 44 may take many forms, such as a donut shape (i.e. having a circular cross-sectional shape) or a bow-tie shape (i.e. having a generally trapezoidal cross-sectional shape) or many others. The balloon 44 increases the area of wall 12 that is engaged for delivery of a fastener 54, and provides an area between distal end 46 and wall 12 within which an anchor can be positioned. This facilitates deployment of the fasteners 54 at favorable angles, as will be described in more detail below.

Figure 5:
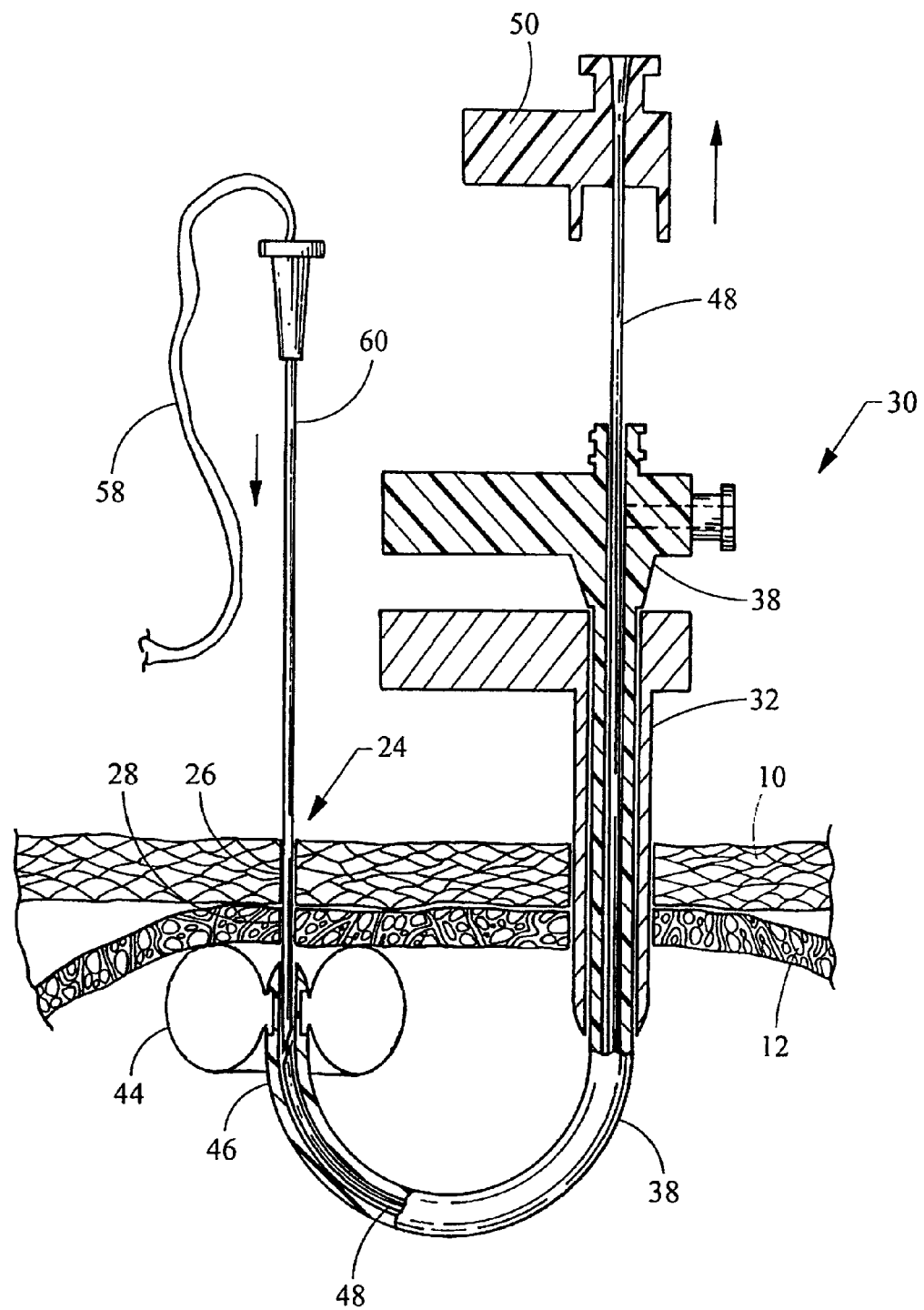

As shown in FIGS. 4 and 5, the distal end 46 of the guide tube 38 and its balloon 44 are laterally spaced from the access cannula 32 and positioned against the gastric wall 12 for placement of a fastener 54. When image guidance is not used, the guide tube 38 may be retracted to a point where the abdominal wall 10 is sufficiently raised to identify the location of the distal end 46. A flexible puncturing device 48 is inserted through the lumen 40 of the guide tube 38 and then passed through the gastric wall 12 and stomach wall 10 to form a second puncture site 24 having openings 26, 28 in the abdominal and gastric walls 10, 12, respectively. Preferably, the flexible puncturing device 48 includes a handle 50 at its proximal end to assist in manipulation of the puncturing device 48, and also includes a sharp taper 52 at its distal end for piercing the bodily walls. The flexible puncturing device 48 is directed generally perpendicular to the surfaces of the walls 10, 12, resulting in the fasteners being placed through the walls at favorable angles. The high level of control provided by the medical device 30 thus ensures that a minimal number of fasteners can be used.

Various fasteners may be used to maintain the wall apposition, and one preferred fastener is a tissue fastener or T-fastener 54 having an anchor 56 and connected suture 58, as is well known in the art. An exemplary T-fastener is shown in U.S. Pat. No. 5,123,914 and sold by Cook Incorporated, Bloomington, Ind., and Wilson-Cook Medical Inc. d/b/a Cook Endoscopy, Winston-Salem, N.C., the disclosure of which is incorporated herein by reference in its entirety. As shown in the figures, the flexible puncturing device 48 is preferably a hollow puncturing needle which defines a lumen sized to receive the anchor 56 of the T-fastener 54. The flexible puncturing needle 48 and anchor 56 preferably have a friction fit, whereby the flexible puncturing needle 48 is retracted from the position shown in FIG. 4, with the anchor inside the hollow tip of the puncturing needle 48, to pull the anchor 56 through the puncture site 24 and into the guide tube 38. Alternatively, the fastener 54 may include its own pushing needle 60, as depicted in FIG. 5. In this case, the anchor 56 may be positioned within the T-fastener pushing needle 60, which in turn is connected to the flexible puncture needle 52 and together guide the anchor 56 through the puncture site 24 and into the gastric lumen. Here, the T-fastener pushing needle can also be positioned inside the hollow tip of the puncturing needle 48. In either case, the flexible puncturing device 48 and/or the guide tube 38 serve as a guide to the fastener, which is then secured as is shown in FIG. 6.

It will be recognized by those skilled in the art that numerous types of fasteners for maintaining wall apposition of two bodily walls are known in the art, and the medical device and/or fastener can be readily configured to suitably connect the flexible puncturing device to the fastener or otherwise guide their placement through the second puncture site 24 and through the opening 26, 28 formed in the abdominal and gastric walls 10, 12. That is, fasteners/anchors and flexible puncturing devices may be specially designed to include suitable connection features, although the use of existing devices as described above is preferred. The fasteners could also be fed through the guide tube 38 and/or puncture needle 48 so that the connector is placed outside abdominal wall 10.

Figure 6:
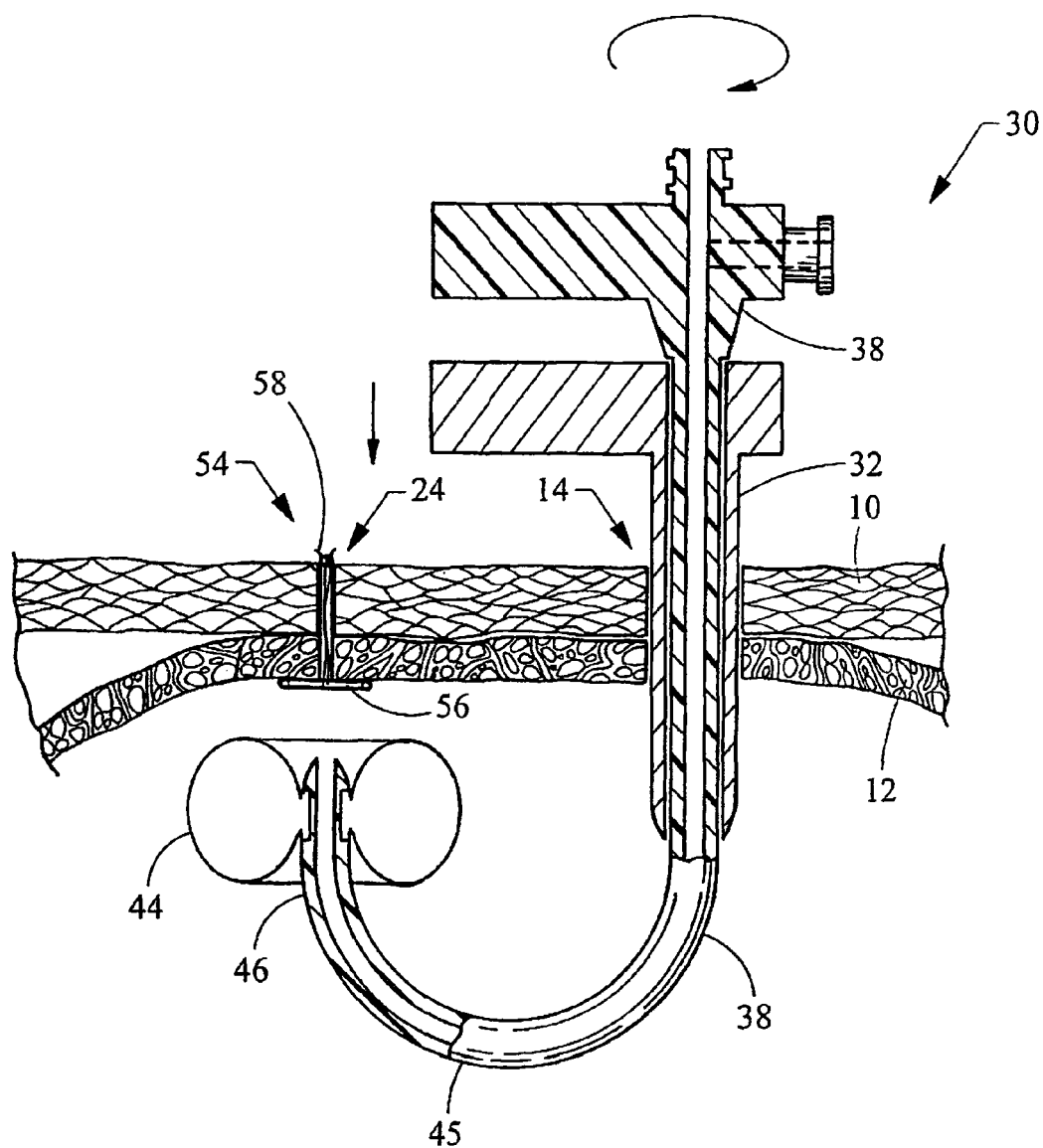
Figure 7:
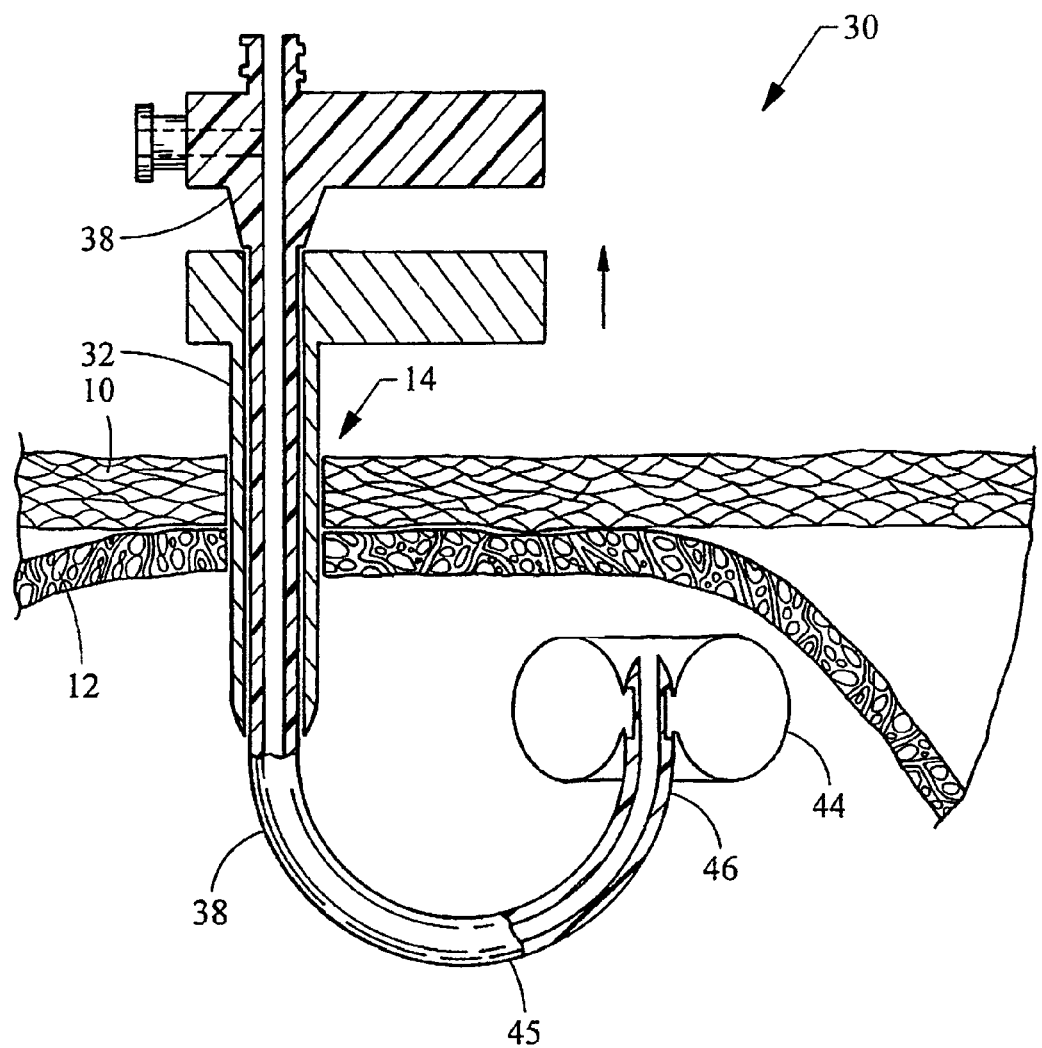
FIG. 7 is cross-sectional view illustrating the placement of an additional fastener.
Figure 8:
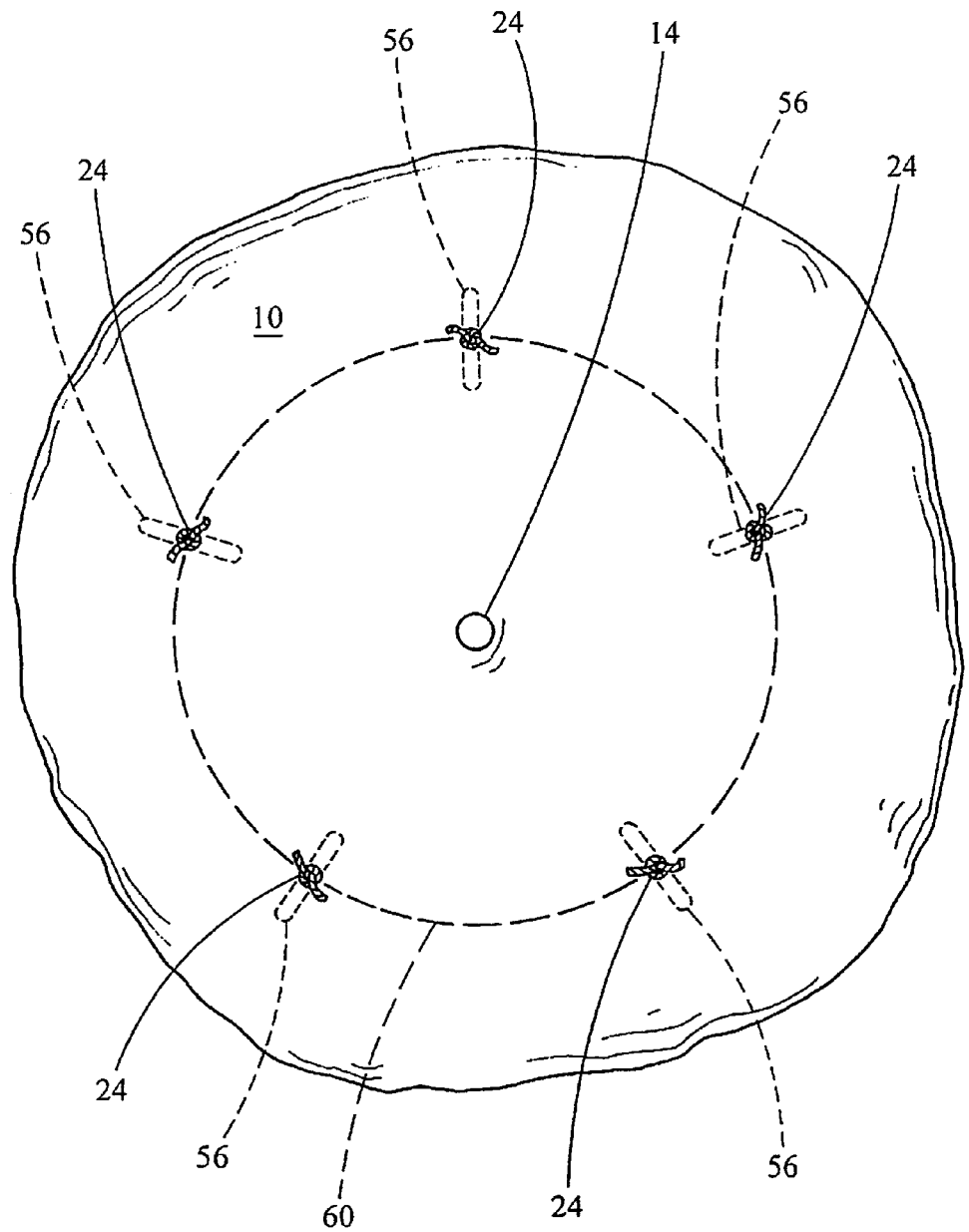
FIG. 8 is a plan view schematically illustrating the placement of several fasteners utilizing the medical device and method of the present invention.

Upon placement of the fastener 54 at the second puncture site 24 (FIG. 6), the device 30 (or at least the guide tube 38) may again be advanced to move the distal end 46 and balloon 44 away from the gastric wall 12, as shown in FIG. 6. Then, the device 30 is rotated (i.e. spun about the axis of access cannula 32), as indicated by the curved arrow. The device 30 is then retracted again to position the distal end 46 and balloon 44 proximate the gastric wall 12 for delivery of a second fastener. As shown in FIGS. 6 and 7, the balloon 44 may remain inflated during repositioning of the guide tube 45. Alternatively, the balloon 44 may be deflated during advancement and rotation of the device 30, and then reinflated once the distal end 46 is positioned at the next puncture site. As shown in the schematic of FIG. 8, utilization of this medical device 30 and the described procedure results in a plurality of puncture sites 24 being formed around the first puncture site 14 along a generally circular path, as indicated by the dotted line 60. While five puncture sites 24 have been depicted, it will be recognized that any number of sites 24 and fasteners 54 may be used depending upon the particular situation.

Upon obtaining wall apposition through the placement of a plurality of fasteners 54, the puncturing device 48, guide tube 38, and access cannula 32 may be removed and a gastrostomy tube (not shown) placed at the first puncture site 14. Accordingly, it will be recognized that the present invention also includes a medical kit for placement of a gastrostomy tube, the kit comprising a first puncture device, a wire guide, a dilator, an access cannula, a guide tube operable between the first linear configuration and the second non-linear configuration, a second flexible puncturing device, at least one fastener, and a gastrostomy tube.

By way of the present invention, reliable and secure percutaneous placement of fasteners are provided through two bodily walls. Through use of the medical device and method, puncturing of the walls is provided at favorable angles resulting in reliable and accurate orientation of the fastener. Likewise, the location of the plurality of puncture sites and fasteners are precisely located with respect to one another. That is, by utilizing the initial gastrostomy puncture site for deployment, a relatively static reference point is provided for placement of the fasteners. In this fashion, only a minimum number of fasteners need to be employed, and their efficacy is maximized.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for providing apposition of two bodily walls, the method comprising the steps of:
   a) forming a puncture site through the two walls;
   b) inserting an access cannula into the puncture site;
   c) passing a guide tube through the access cannula, the guide tube retroflexing after passing beyond a distal end of the access cannula;
   d) positioning a distal end of the guide tube proximate one of the bodily walls;
   e) passing a flexible puncturing device through the guide tube and puncturing the two bodily walls at a second location;
   f) connecting a fastener to the puncturing device;
   g) retracting the puncturing device to draw the fastener through the two bodily walls at the second location; and
   h) securing the fastener to maintain apposition of the two walls at the second location.

2. The method of claim 1, wherein step d) includes retracting the guide tube to engage one of the walls at a desired location.

3. The method of claim 2, further comprising the steps of:
   i) advancing the guide tube to disengage the bodily wall at the second location;
   j) rotating the guide tube; and
   k) retracting the guide tube to position the distal end of the guide tube proximate the bodily wall at a third location.

4. The method of claim 1, wherein steps d)-h) are repeated with a second fastener at a third location.

5. The method of claim 1, wherein steps d)-h) are repeated with a plurality of fasteners that are placed in a generally circular configuration around the puncture site.

6. The method of claim 1, wherein the positioning step includes inflating a balloon at the distal end of the guide tube.

7. The method of claim 6, wherein the balloon is pressed against one of the bodily walls.

8. The method of claim 1, wherein the flexible puncturing device comprises a flexible puncturing needle, and wherein the connecting step includes positioning an anchor of the fastener within the flexible puncturing needle.

9. The method of claim 1, further comprising the steps of:
   i) removing the puncturing device, guide tube, and access cannula; and
   j) placing a gastrostomy tube at the puncture site.

10. The method of claim 1, wherein step g) includes retracting the puncturing device such that the fastener moves from a proximal side of the two bodily walls to a distal side of the two bodily walls.

11. The method of claim 1, wherein the guide tube is operable between a first linear configuration and a second non-linear configuration, the distal end of the guide tube being laterally spaced from the access cannula in the second non-linear configuration.

12. The method of claim 11, wherein the guide tube retroflexes in the second configuration for engagement of one of the bodily walls.

13. The method of claim 11, wherein the distal end of the guide tube in the second configuration is rotated about 180 degrees relative the distal end in the first configuration.

14. The method of claim 11, wherein the distal end of the guide tube faces generally proximally in the second configuration.

15. The method of claim 1, wherein the fastener comprises a tissue fastener having an anchor and suture material, and wherein the flexible puncturing device is a flexible puncturing needle and the anchor is sized to be received within a lumen of the flexible puncturing needle.

* * * * *